(12) United States Patent
Breidenthal et al.

(10) Patent No.: US 9,036,281 B2
(45) Date of Patent: May 19, 2015

(54) OPTO-MECHANICAL DEVICES WITH SHARP-EDGE LENSES

(71) Applicant: Intuitive Surgical Operations, Inc., Sunnyvale, CA (US)

(72) Inventors: Robert S Breidenthal, Bolton, MA (US); Richard Cyr, New Ipswich, NH (US); David Chambers, Warren, MA (US); Joseph N Forkey, Princeton, MA (US); Robert N Ross, Gardner, MA (US); Brian E Volk, Jefferson, MA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 67 days.

(21) Appl. No.: 13/893,470

(22) Filed: May 14, 2013

(65) Prior Publication Data

US 2013/0301149 A1    Nov. 14, 2013

Related U.S. Application Data

(60) Provisional application No. 61/646,769, filed on May 14, 2012.

(51) Int. Cl.
| | |
|---|---|
| *G02B 7/02* | (2006.01) |
| *G02B 23/24* | (2006.01) |
| *A61B 1/00* | (2006.01) |
| *A61B 1/05* | (2006.01) |

(52) U.S. Cl.
CPC ........ *G02B 7/02* (2013.01); *G02B 7/025* (2013.01); *G02B 23/2476* (2013.01); *A61B 1/00096* (2013.01); *A61B 1/05* (2013.01); *A61B 1/0011* (2013.01)

(58) Field of Classification Search
CPC ................................. G02B 7/02; G02B 7/025
USPC ................................................... 359/811, 819
See application file for complete search history.

(56) References Cited

U.S. PATENT DOCUMENTS

| | | | |
|---|---|---|---|
| 7,715,105 B2 | 5/2010 | Forkey et al. | |
| 2001/0033436 A1* | 10/2001 | Hunter | 359/819 |
| 2004/0196569 A1 | 10/2004 | Quake et al. | |
| 2006/0077563 A1 | 4/2006 | Mihara et al. | |

OTHER PUBLICATIONS

Efremov A.A. et al Sborka opticheskikh priborov. moskvsa, "Vysshaya shkola", 1978, p. 144,145.
International Search Report PCT/US2013/050438 dated Nov. 7, 2013.

\* cited by examiner

*Primary Examiner* — William Choi

(57) ABSTRACT

An opto-mechanical device, such as a lens cell, includes a housing having an axially extending chamber and an intermediate internal spacer that positions a sharp-edged lens in the chamber. The sharp-edged lens has first and second optical surfaces that intersect in a circumferential sharp edge. The housing positions an image sensor proximal to the sharp-edged lens for processing light therefrom.

12 Claims, 5 Drawing Sheets

OPTO-MECHANICAL DEVICES WITH SHARP-EDGE LENSES

CROSS REFERENCE TO RELATED APPLICATION

This application claims priority from U.S. Provisional Patent Application No. 61/646,769 for Opto-Mechanical Devices with Sharp-Edged Lenses filed May 14, 2012 and assigned to the same assignee as this invention.

BACKGROUND OF THE INVENTION

1. Field of the Invention

This invention generally relates to opto-mechanical devices for producing images to be displayed and more specifically to opto-mechanical devices for use in procedures requiring miniaturized imaging devices.

2. Description of Related Art

In recent years endoscopic and other like imaging systems have been developed to display an image on a video monitor. These imaging systems typically include opto-mechanical devices with housings for supporting optical devices such as objectives of one or more lenses. An objective forms an image for being conveyed to a remote video processor. In some applications, an image sensor proximate the objective interfaces with the objective and converts the incoming light from the objective into digital signals that are coupled to a video processor. Other applications define an interface for one end of a coherent fiber bundle and an objective; the other end of the bundle terminates with a remote connection to the video processor. In either embodiment glass objectives are preferred for good image quality.

Customers for such devices, particularly in the medical field, also express a desire for imaging systems with minimal cross-sections, particularly systems that can be manufactured at low cost and in high volumes for single-use, disposable instrumentation. Recently imaging sensors have become available with cross-sections of less than 2 mm. and with pixel densities that provide good image resolution. However, prior art optical devices have not been available for interfacing with such image sensors in commercially acceptable production quantities and costs.

As known, the production of a larger, conventional lens involves grinding and polishing end surfaces of an optical glass blank to form two polished spherical optical surfaces spaced along an axis. Each lens then undergoes edge grinding to reduce the lens diameter to a specified value and to align the optical and mechanical axes. U.S. Pat. No. 7,715,105 (2010) to Forkey et al. for an Acylindrical Optical Device discloses an alternative by which small diameter lenses are manufactured from over-sized lens elements and other optical elements formed into lens systems. Edges are sawn into each lens system to reduce its overall size. Sawing can be applied to integral lens elements or lens arrays. As an alternative, lenses also can be molded from glass or plastic. Photolithographic techniques constitute another alternative that can be used to fabricate lenses on a wafer, such as included in an image sensor.

Prior art molding processes become difficult to implement for the production of small lenses with diameters less than 2 mm. It is difficult to obtain acceptable resolution with plastic lenses of this size. Edge grinding, such as used with manufacture of standard lenses, must be undertaken with tighter controls for increased accuracy. Edge grinding is also time-consuming and therefore increases manufacturing costs. The above mentioned sawing process may not be appropriate for newer applications, particularly those which require high-volume, low cost production. Lithographic processes can be applied only to a limited number of materials and have limited radii of curvature. Consequently they are unlikely to provide a lens with a high index of refraction and/or short radius of curvature as is required for obtaining a large field of view with small lenses.

What is needed is an opto-mechanical assembly constructed with a diameter of in the order of 2 mm or less that can interface with a small image sensor or coherent fiber bundle wherein the opto-mechanical assembly can be provided in sufficiently large volumes and at sufficiently low costs such that instruments incorporating such assemblies can be made as disposable instruments or components thereof.

SUMMARY

Therefore it is an object of this invention to provide an opto-mechanical assembly to be constructed with a small glass lens for being interfaced with components for conveying an image to a remote image processor.

Another object of this invention is to provide an opto-mechanical assembly with a small glass lens and an image sensor at reasonable production costs at high volumes.

Still another object of this invention is to provide an opto-mechanical assembly with a small glass lens and an interface for a coherent fiber bundle for conveying an image to a remote image processor at reasonable production costs and high-volumes.

In accordance with one aspect of this invention an opto-mechanical assembly comprises a lens having first and second polished surfaces that intersect in a sharp edge at the periphery thereof. A support carries the lens.

In accordance with another aspect of this invention, an opto-mechanical assembly comprises a lens having first and second polished surfaces that intersect in a sharp edge at the periphery thereof. A support in form of a housing carries the lens. A processor supported by the housing receives light from the lens and the housing includes a structure that positions the lens and the processor in an operative relationship.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
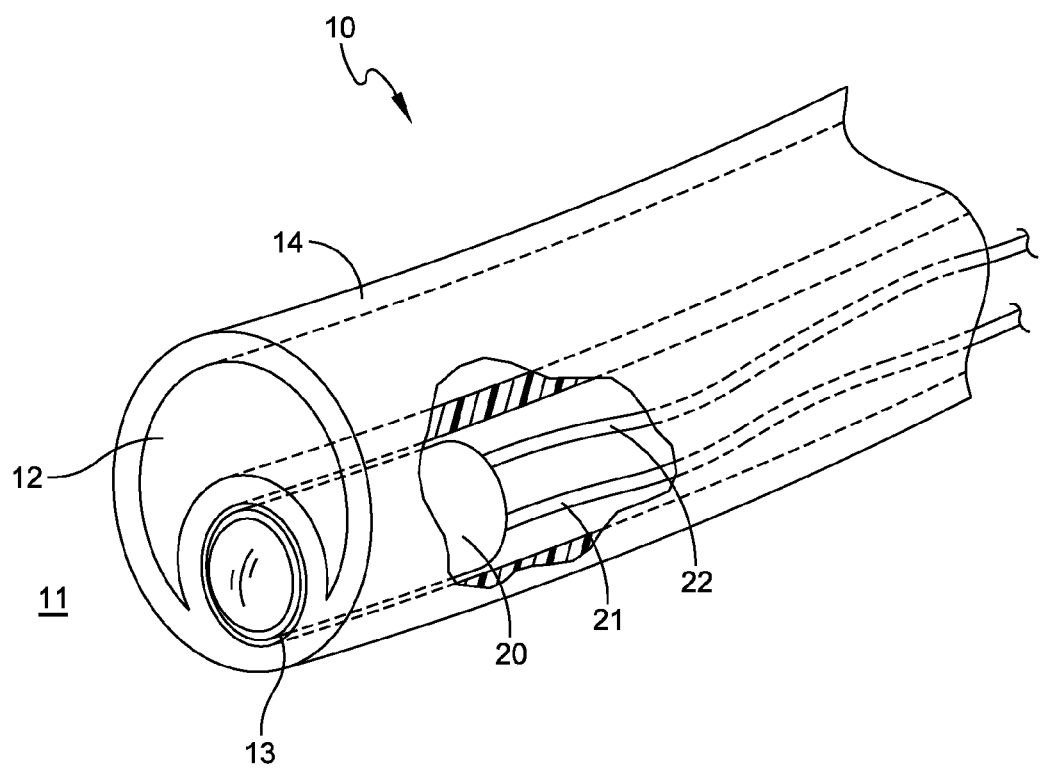
FIG. 1 is a perspective view of a portion of an endoscope thereof taken from the distal end with an opto-mechanical assembly in the form of a lens cell that can incorporate this invention.

FIG. 1 discloses a portion of an endoscope 10 viewed from a distal end 11 that depicts an illumination channel 12 and an imaging lumen 13 within a flexible sheath 14. A portion of the sheath 14 is cut away to display an opto-mechanical assembly in the form of a lens cell 20 that includes imaging optics and an image sensor that connects through conductors 21 and 22 to an electronic imaging system (not shown) that processes and displays the image formed by an objective in the lens cell 20. Such electronic imaging systems are well known in the art.

Figure 2:
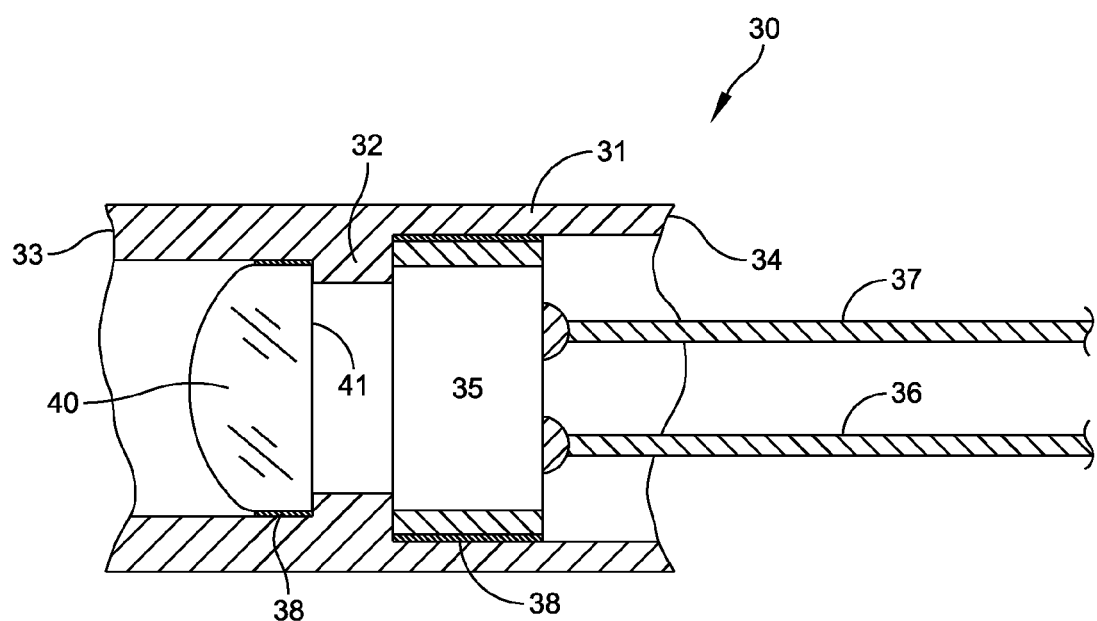
FIG. 2 is a cross-section of a prior art opto-mechanical device.

FIG. 2 discloses a lens cell 30 including a prior art opto-mechanical device. A housing 31, which may have a cylindrical or other cross-section, includes an integral annular positioning band 32 that is intermediate distal and proximal portions 33 and 34. An image sensor 35 with its conductors 36 and 37 abuts a proximal shoulder formed by the annular band 32. A conventional plano-convex lens 40 has its planar surface 41 abutting a distal shoulder on the annular band 32. Adhesive material 38 in peripheral gaps between the housing 31 and each of the image sensor 35 and lens 40 provides axial component stability. The distance between the lens 40 and the imaging sensor 35 is based upon the focal length of the lens 40 and the particular application for the instrument containing the opto-mechanical device 30. Methods for determining such spacing are well known to those of ordinary skill in the art.

Figure 3:
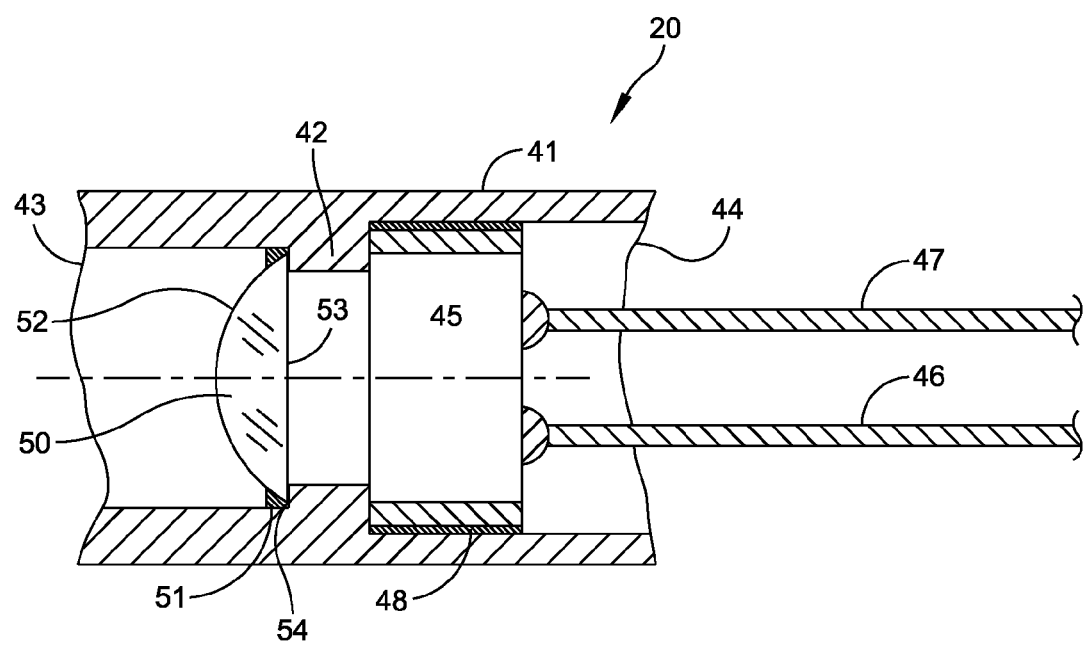
FIG. 3 is a cross-section of one embodiment of an opto-mechanical device that incorporates a sharp-edged plano-convex lens of this invention.

As previously indicated, opto-mechanical devices, such as the device 30, are difficult to manufacture as the diameters of the lens and housing reduce into the range of 2 mm or less. FIG. 3 depicts a cross-section of one embodiment of the lens cell 20 in FIG. 1 that incorporates this invention. This lens cell 20 includes a lens support in the form of a housing 41 with an annular positioning band 42 that is intermediate distal and proximal portions 43 and 44. In this embodiment a commercially available small image sensor 45 is positioned against a proximal shoulder of the annular positioning band 42. Conductors 46 and 47 provide an interface between the image sensor 45 and remote image processing equipment and correspond to the conductors 21 and 22 in FIG. 1.

Still referring to FIG. 3, an objective lens 50 is positioned against the distal shoulder of the annular band 42 and held in place with adhesive material 51 about the periphery of the lens 50. The objective lens 50 in this particular embodiment is a plano-convex lens with a convex polished surface 52 facing distally and a planar polished surface 53 facing proximally toward the image processor 45.

The objective lens 50 is a sharp-edged lens. Specifically, it is a lens formed by two optical surfaces 52 and 53 that intersect at an angle thereby forming a sharp edge 54 about the periphery of the lens which has not been subjected to any edge grinding. Thus, the manufacturing of the sharp-edged lens 50 of FIG. 3 avoids the expense and time for edge grinding that would otherwise be required to reduce the diameter of a lens into the range of 2 mm or less. Moreover a sharp-edged lens, such as the objective lens 50, is self centering. That is, during manufacture the intersection of the optical surfaces generates an outside diameter that is automatically aligned with the center of the optical surfaces. It will also be apparent that only a minimal effort is required to secure the lens 50 into the housing 41, as by the simple application of adhesive material 51.

Sharp-edged lenses have not been widely adopted in optics manufacturing. This is, in part, due to the potential that small shocks can cause the sharp edge of a larger lens to break. However, small sharp-edged lenses to which this invention is directed have a smaller mass. Two other factors are involved. First, circumference is proportional to lens diameter. Force on a lens due to shock is proportional to the mass of the lens which, in turn, is approximately proportional to the diameter, d, of the lens cubed (i.e., $d^3$). Force per unit length of a sharp edge at the lens periphery is proportional to the diameter squared (i.e., $d^2$). Consequently as the diameter of a lens decreases into the range at which this invention is directed, the force per unit length at the sharp edge decreases dramatically and a sharp-edge lens having a diameter in a range of less than 2 mm can withstand normally encountered adverse effects of shocks and other forces.

Figure 4:
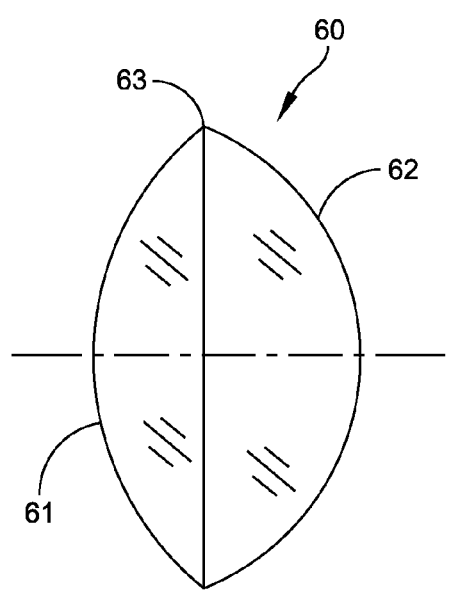
FIG. 4 is a plan view of a sharp-edged bi-convex lens that could be incorporated in other opto-mechanical devices.
Figure 5:
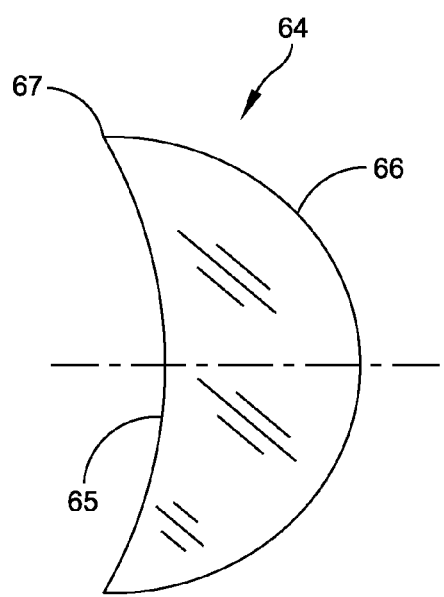
FIG. 5 is a plan view of a sharp-edged concave-convex lens that could be incorporated is still other opto-mechanical devices.

Other lens shapes can be used with the same benefits for other applications. FIG. 4, for example, depicts a view of a biconvex lens 60 that has spherical optical surfaces 61 and 62 that intersect along a sharp edge 63. FIG. 5 depicts a concave-convex lens 64 with a concave polished surface 65 and a convex polished surface 66 that form a sharp edge 67.

Figure 6:
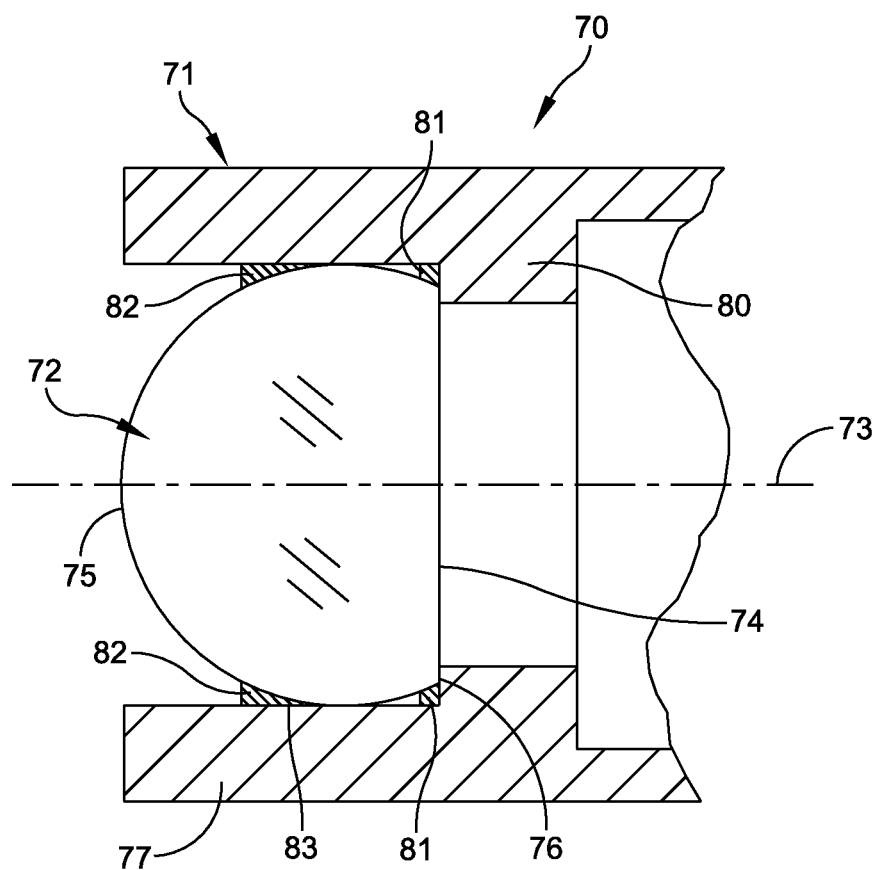
FIG. 6 is a cross-section view of another embodiment of an opto-mechanical device that utilizes a convex-plano lens carried by a support in the form of a housing.

FIG. 6 depicts an opto-mechanical device 70 with a support 71 for carrying a convex-plano lens 72 on an axis 73 in accordance with this invention. A knife edge 76 is formed about the periphery of the lens 72 at the intersection of the polished planar surface 74 and the adjacent surface of the spherical portion 75 of the lens 72. The device 70, such as shown in FIG. 6, can include a tubular housing 77 with an internal circumferentially extended annular shoulder 80. Adhesive 81 can be applied to the radial shoulder surface against which the peripheral portion of the planar surface is pressed to lock the lens 72 in place. Alternatively or in addition, adhesive 82 could be applied to the lens 72 and housing 77 at a gap 83 proximate a point of contact between lens 72 and the housing 77.

As now will be apparent, an opto-mechanical assembly or lens cell in accordance with this invention includes a sharp-edged lens and interface for conveying the image to a remote image processing system. The use of sharp-edged lenses enables the manufacture of such lens cells in high volumes and at low cost. This could be particularly important in designing a lens cell, such as the lens cell 20 in FIGS. 1 and 3, at a sufficiently low cost to justify its inclusion in a disposable instrument thereby significantly reducing cleaning costs that are otherwise required in the medical and other fields. Such an assembly can be constructed with an interface to an image sensor included with the assembly or to a coherent fiber bundle as will be apparent to those skilled in the art.

This invention has been disclosed in terms of certain embodiments. Many modifications can be made to the disclosed apparatus without departing from the invention. For example, this application shows several embodiments of sharp-edged lenses useful in accordance with this invention. Embodiments with other configurations could be substituted. Specific cylindrical housing configurations have been disclosed; alternative housing configurations could be substituted. Therefore, it is the intent of the appended claims to cover all such variations and modifications as come within the true spirit and scope of this invention.

What is claimed as new and desired to be secured by Letters Patent of the United States is:

1. An opto-mechanical assembly comprising:
   A) a lens having a diameter of less than about 2.0 mm and wherein such lens further has first and second polished surfaces that intersect in a sharp edge at the periphery thereof, and
   B) a support that carries said lens.

2. The opto-mechanical assembly as recited in claim 1 wherein said first and second polished surfaces define a lens taken from the group consisting of plano-convex, concave-convex and biconvex lenses.

3. The opto-mechanical assembly of claim 1 wherein said support includes an integral annual positioning band for positioning said lens in said support.

4. The opto-mechanical assembly of claim 3 additionally including adhesive about the periphery of said lens thereby to secure said lens in said support.

5. An opto-mechanical assembly comprising:
A) a lens having a diameter of less than about 2.0 mm and wherein such lens further has first and second polished surfaces that intersect in a sharp edge at the periphery thereof,
B) a housing that caries said lens,
C) processing means mounted to said housing for receiving light from said lens, and
D) means for positioning said lens and said processing means with respect to said housing in an operative relationship.

6. The opto-mechanical assembly as recited in claim 5 wherein said first and second polished surfaces define a lens taken from the group consisting of plano-convex, concave-convex, and biconvex lenses.

7. The opto-mechanical assembly as recited in claim 5 wherein said positioning means includes an integral annular positioning band in said housing that defines a shoulder for positioning said lens within said housing.

8. The opto-mechanical assembly as recited in claim 7 additionally including adhesive about the periphery of said lens thereby to secure said lens in said housing against a first shoulder.

9. The opto-mechanical assembly as recited in claim 7 wherein said first and second polished surfaces define a lens taken from the group consisting or plano-convex, concave-convex, and biconvex lenses.

10. The opto-mechanical assembly as recited in claim 5 wherein said positioning means includes an integral annular positioning band in said housing with first and second shoulders for positioning said lens and said processing means in a spaced relationship within said housing.

11. The opto-mechanical assembly as recited in claim 10 additionally including adhesive about the peripheries of said lens and said processing means to secure said lens and said processing means in said housing against first and second shoulders, respectively.

12. The opto-mechanical assembly as recited in claim 10 wherein said first and second polished surfaces define a lens taken from the group consisting of plano-convex, concave-convex, and biconvex lenses.

* * * * *